United States Patent
Wakabayashi

(10) Patent No.: US 7,013,890 B2
(45) Date of Patent: Mar. 21, 2006

(54) BRONCHIAL TUBE WITH AN ENDOBRONCHIAL Y-GUIDE

(75) Inventor: Akio Wakabayashi, Garden Grove, CA (US)

(73) Assignee: CMS Surgical, Inc., Laguna Hills, CA (US)

( * ) Notice: Subject to any disclaimer, the term of this patent is extended or adjusted under 35 U.S.C. 154(b) by 0 days.

(21) Appl. No.: 10/224,089

(22) Filed: Aug. 20, 2002

(65) Prior Publication Data
US 2004/0035429 A1 Feb. 26, 2004

(51) Int. Cl.
*A61M 16/00* (2006.01)
(52) U.S. Cl. .............. 128/200.26; 606/108; 128/207.15
(58) Field of Classification Search ................ 606/108, 606/191–200; 604/96.01–109; 128/200.2, 128/200.26, 204.18, 207.14–207.18
See application file for complete search history.

(56) References Cited

U.S. PATENT DOCUMENTS

| | | | | | |
|---|---|---|---|---|---|
| 2,541,402 | A | * | 2/1951 | Caine | 128/200.26 |
| 4,819,664 | A | * | 4/1989 | Nazari | 128/207.15 |
| 4,840,172 | A | * | 6/1989 | Augustine et al. | 128/207.14 |
| 5,588,424 | A | * | 12/1996 | Insler et al. | 128/207.15 |
| 5,669,924 | A | * | 9/1997 | Shaknovich | 623/1.11 |
| 5,720,735 | A | * | 2/1998 | Dorros | 604/284 |
| 2002/0143380 | A1 | * | 10/2002 | Dahl et al. | 607/122 |

* cited by examiner

*Primary Examiner*—Glenn K. Dawson
(74) *Attorney, Agent, or Firm*—Willie Krawitz

(57) ABSTRACT

A non-slip, bronchial tube is provided for insertion into the trachea for chest surgery purposes. Insertion is accomplished through a conventional endotracheal tube by means of a built-in, spring loaded stylet. An endobronchial tube is attached to the end of the bronchial tube and is configured as a Y-guide having expandable left and right arms which are glued or welded to join a central portion. The spring loaded stylet is mounted within the central portion. A spring loading at the end of the bronchial tube is secured within a sheath mounted along the distal end of one arm, typically along the left arm, and this spring loading is secured within an inflatable cuff. When the bronchial tube is inserted through the endotracheal tube by means of the stylet, the Y-guide which is attached to the bronchial tube will also move forward causing the arms of the Y-guide to press lightly against the carina of the trachea-bronchial tree and separate into the left and right bronchia. When the cuff is inflated, the left bronchial lumen is isolated from the trachea-right bronchial space and can be left open to the atmosphere without slippage which enables oxygen and anesthetic gas to be ventilated only into the right lung during surgery. After surgery, the cuff is deflated and the device is removed with the stylet.

12 Claims, 4 Drawing Sheets

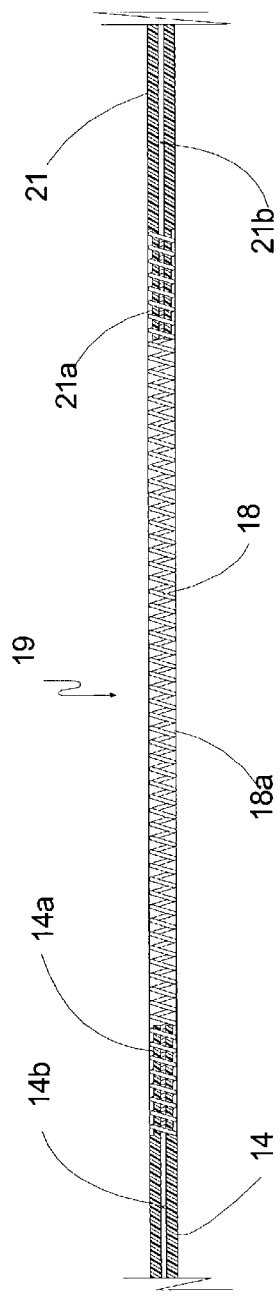
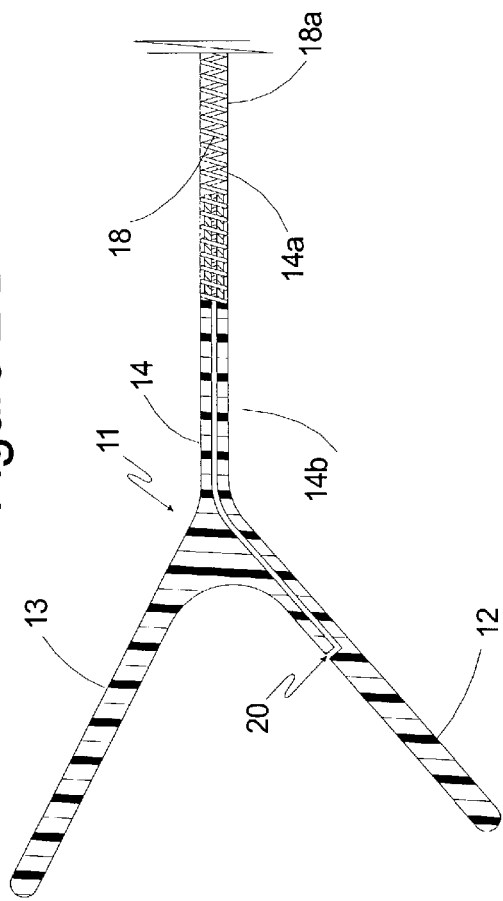
Figure 2 B
Figure 2 A

BRONCHIAL TUBE WITH AN ENDOBRONCHIAL Y-GUIDE

BACKGROUND OF THE INVENTION

This device relates to a new and improved bronchial tube with a built-in stylet and Y-guide which leads the endobronchial portion into the left bronchus and prevents slippage from the left bronchus.

In order to perform endoscopic surgery inside the chest cavity, the lung of the operative side must be collapsed, while the other side of the lung is ventilated with oxygen and anesthetic gas, and this technique is referred to as one-lung ventilation. Other types of thoracic surgery such as a lobectomy for lung cancer through a standard open incision (thoracotomy) are also greatly facilitated by one-lung ventilation, i.e., separating the air flow from the trachea into the right and left bronchi, followed by collapse of the appropriate lung.

For many decades, a double lumen endobronchial tube known as the 'Robert Shaw' tube has been employed consisting of a thick plastic tube divided into two channels by a septum. One channel opens at the end and the other opens several centimeters proximal to the tip. When the tip is inserted into one bronchus for collapsing the lung, the other bronchus can receive oxygen and gas through the side.

But, the "Robert Shaw" type of tube is difficult to properly position in the bronchus since it has two curves, and must be twisted inside the trachea in order to properly place the tip inside the left bronchus. Also, the device frequently tends to slip out of the left bronchus and enter the right bronchus when the patient is placed from a supine position at commencement of anesthesia to a lateral position for surgery, or the head position is changed.

THE INVENTION

According to the invention, there is provided an endobronchial tube connected to a bronchial tube, the endobronchial tube being configured as a Y-guide comprising two flexible arms which are attached to a central hollow portion. Following insertion of a standard endotracheal tube into the patient, the bronchial tube is advanced by a built-in, flexible, polymeric stylet through the endotracheal tube until the arms of the Y-guide emerge from the endotracheal tube to expand and contact the carina. The two arms of the Y-guide then separate at the carina due to their flexibility or spring action, and enter into each corresponding bronchus. Typically, the left bronchus arm of the Y-guide is stabilized inside the left bronchus by a spring mounted between the Y-guide and the stylet.

When the Y-guide is pushed lightly against the carina, securement by the spring loading enables the endobronchial tube to remain in place, without slippage regardless of the patient's head position during anesthesia.

BRIEF DESCRIPTION OF THE DRAWINGS

FIG. 2A is a cross section plan view of the Y-guide portion and spring loaded advancing stylet;

FIG. 2B is a cross section view in side elevation showing the spring coil stabilizer with a thin wall polymer sheath interposed between the central position of the Y-guide and the distal end of a hollow flexible stylet;

DESCRIPTION OF THE PREFERRED EMBODIMENTS

Figure 1:
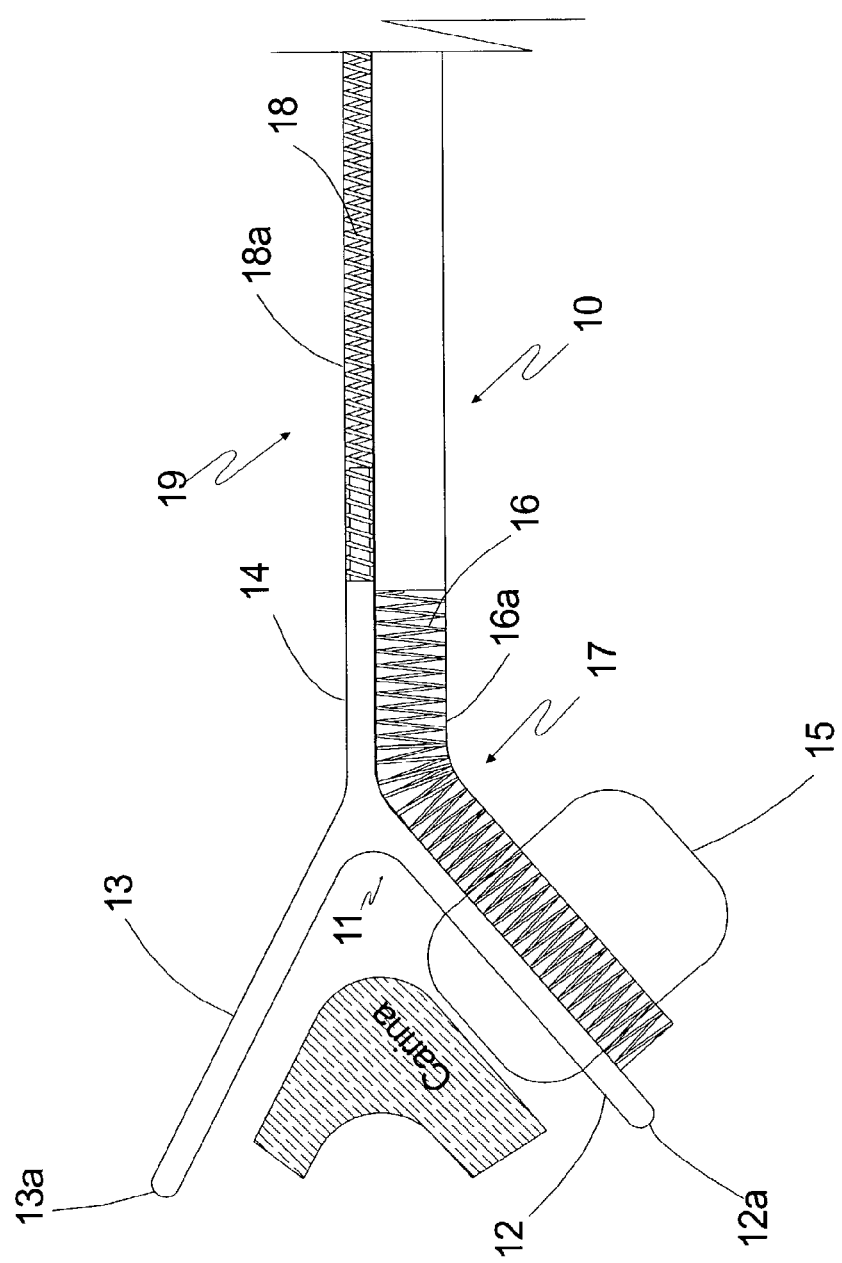
FIG. 1 is a plan view of the assembled endo-bronchial tube with the Y-guide of this invention.

The bronchial tube 10 of this invention shown in FIG. 1 is constructed of a thin polymer such as polyurethane, silicone rubber, or other compatible elastomers and attached at its end to an endobronchial tube 17. A Y-guide 11 is attached at its end to the endobronchial tube, and the Y-guide defines end tapered left arm 12 and closed left arm 13. FIGS. 1, 2A and 2B, show the Y-guide which includes a tubular, tapered central arm 14 that is inserted into a stabilizer 19 comprising a spring coil 18 covered with a thin polymer sheath 18a. The spring stabilizer forms part of a stylet shaft 21 which will be described more fully in FIG. 3D. The endobronchial tube itself is constructed of a thin wall elastic polymer such as silicone rubber, PVC, polyurethane, or other compatible elastomers, and reinforced with a metal coil 16, as shown, or a stiff polymer, etc. The two arms 12 and 13 may be integrally formed with the tapered central arm 14, or they may be connected to the central arm by gluing, heat sealing, etc. An air expandable cuff 15 is attached near the end of left arm 12 and the cuff partially encloses the metal coil 16 which is contained within a flexible polymer sheath 16a. The metal coil 16 extends along the left arm 12 and central arm 14 of the Y-guide 11 to the distal end of the bronchial tube 10 and prevents collapse of the endobronchial tube when the cuff 15 is inflated. The metal coil reinforcement 16 also prevents kinking of the endobronchial tube at the bending portion along the Y-guide.

Inflating the cuff 15 via an air bore 20 will separate the left bronchial lumen and the right bronchial lumen. The spring coil 18 of the stabilizer 19 enables the Y-guide 11 to be lightly pushed against a patient's carina. As indicated, the spring coil 18 is secured within the thin polymer sheath 18a, while the tapered end of the Y-guide enables fitting into the end of the spring coil. A hollow, sponge-like porous material has the potential to replace the metal coil. FIG. 2B shows a tapered end of the hollow stylet shaft 21 inserted into stabilizer 19.

Figure 3:
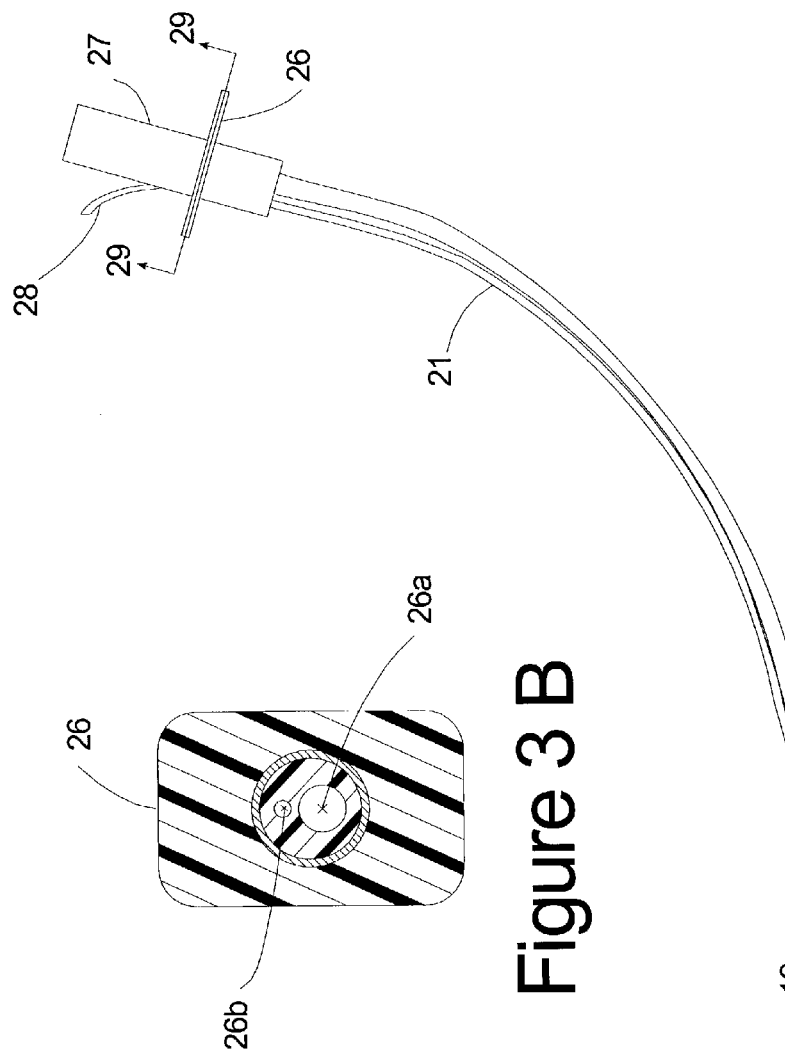
FIG. 3A is a plan view of the assembled bronchial tube.
FIG. 3B is a cross section view of the bronchial tube connector taken along lines 29—29 of FIG. 3A.
FIG. 3C is cross section view in side elevation showing the folded Y-guide being advanced through the endotracheal tube; and, FIG. 3D is a cross section view in side elevation showing the expanded Y-guide after emerging from the endotracheal tube.
Figure 3:
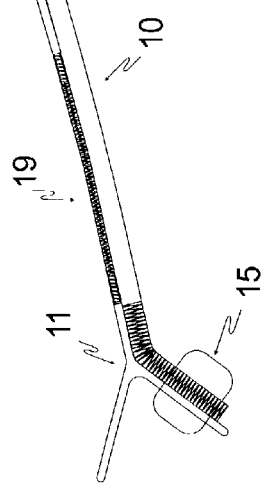

FIG. 3A shows the assembled bronchial tube 10 and attached Y-guide 11, stabilizer 19, built-in stylet shaft 21 and a bronchial tube connector 27. FIG. 3B shows a cross section of the bronchial connector taken along lines 29—29 of FIG. 3A which separate the bronchial tube 10 and the stylet shaft 21. As shown in FIGS. 3A and 3B, an air channel 26b of the stylet is connected to an air tube 28, a bronchial tube lumen 26a is connected to a ventilator through the bronchial tube connector 27 and a plate 26 functions to facilitate handling of the device.

Figure 3C:
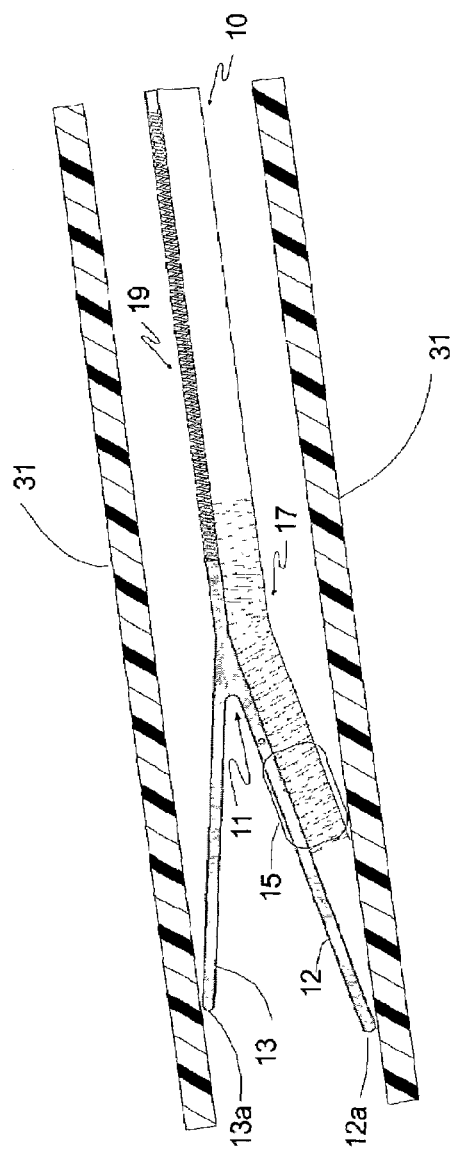

As shown in FIG. 3C, with the balloon cuff 15 deflated, the Y-guide is inserted into a standard endotracheal tube 31, and the flexible arms 12 and 13 become somewhat closed. Movement of these closed arms through the endotracheal tube is facilitated by end rounding 12a and 13a of the two arms 12, 13.

Figure 3D:

When the flexible Y-guide arms emerge from the endotracheal tube, as shown in FIG. 3D, their outward flexibility will cause the two arms to separate once inside the trachea.

Hence, upon contact with the carina, the separated arms 12 and 13 of the Y-guide will be deflected by the carina and enter into their respective left and right bronchi automatically due to this outward flexibility. In the embodiment shown, and with the right arm 13 always being closed, the balloon cuff 15 is then inflated from the air tube 28, through the hollow stylet 21 and outlet 20. This will enable the left bronchial lumen to be separated from the trachea-right bronchial lumen; ventilation to the right bronchus is maintained through the endotracheal tube 31.

Initially, ventilation to the bronchial tube 10 is provided through the proximal end of the bronchial tube connector 27, but when the bronchial tube connector is disconnected from the ventilator, the left lung becomes open to ambient air. Hence, when the surgeon then opens the chest cavity wall, cavity air pressure will become unbalanced, and air will flow into the chest cavity causing the left lung to collapse. However, ventilation to the right side of the bronchus and to the right lung will still be maintained through the endotracheal tube 31 (FIGS. 3C and 3D).

Since securement of the device within the left bronchus is effected by a spring stabilizer rather than requiring a stiffer and hence thicker polymeric tube, a thinner wall thickness may be used for the bronchial tube. This enables the bronchial tube of this invention to be constructed with an inside diameter which typically may vary from about 3.8 mm–4.9 mm, and an outside diameter of about 4.3 mm–5.4 mm. These inside dimensions are quite sufficient for a bronchoscope having an outside diameter of say 3.5 mm–3.7 mm to easily pass through the device for examination purposes.

Additionally, since the spring stabilizer enables use of a shorter left end of the endobronchial tube, this in turn will significantly reduce hospital inventory requirements since one size of the endobronchial tube of this invention can cover a much wider range of patient's sizes than existing endobronchial tubes.

Moreover, since the bronchial tube of this invention provides a built-in stylet, it functions to facilitate insertion, maintains the endobronchial tube in place without slippage, and the stylet serves as an air channel to the balloon cuff.

Presently existing endobronchial tubes employ an introducing stylet constructed of aluminum, and the stylet must be removed after the tube is inserted into the trachea. By comparison, instead of using an aluminum stylet, the polymeric stylet of this invention is sufficiently flexible to move through the endotracheal tube and, the present stylet does not require a possible readjustment and reinsertion compared to an aluminum stylet.

On an operational basis, since the air pressure inside the bronchial tube is always positive during a ventilation cycle, it is not necessary to make the wall of a bronchial tube thick and stiff, and this facilitates insertion of the bronchial tube through a standard endotracheal tube 31, and this aspect is shown in FIG. 3C.

It will be appreciated that a similar configuration of the endobronchial tube and Y-guide can be adapted for use in the right bronchus.

The invention claimed is:

1. A bronchial tube with an endobronchial Y-guide device for insertion through an endotracheal tube, and into a patient's tracheal tree, including left and right bronchi, left bronchial lumen, carina, and left bronchial space of a patient, comprising;
   a.) a bronchial tube;
   b.) Y-guide mounted at the distal end of the bronchial tube, the Y-guide defining outwardly oriented, flexible left and right arms joined to a central tube portion defining an open proximal end;
   c.) a flexible, polymeric, hollow stylet shaft defining distal and proximal ends built into and coextensive with the bronchial tube, the Y-guide mounted at the proximal end of the central tube portion to the distal end of the stylet;
   d.) biasing means between the stylet and the central tube portion of the Y-guide;
   e.) an enclosed reinforcement mounted along the left arm and extending along the central tube to the distal end of the bronchial tube, the reinforcement preventing distortion of the Y-guide during use;
   f.) an expandable cuff mounted along the left arm of the Y-guide and which at least partially surrounds the enclosed reinforcement and the left arm; whereby,
      i. when the bronchial tube is inserted through the endotracheal tube, the left and right arms of the Y-guide are compressed for passage therethrough;
      ii. when the Y-guide emerges from the endotracheal tube, the left and right arms of the Y-guide are outwardly expanded to their initial outward orientation;
      iii. when the expanded arms of the Y-guide are moved by the stylet into contact with the carina, the arms will separate into the respective left and right bronchi;
      iv. inflation of the cuff through the stylet will secure the left arm of the Y-guide to the left bronchus and isolate the left bronchial lumen from the tracheal-bronchial space, thereby opening the left bronchus to atmospheric, and enabling oxygen and anesthetic gas to be ventilated only into the right lung during surgery; and,
      v. upon completion of surgery, the cuff is deflated and the device is removed from the patient.

2. The device of claim 1, in which the inside diameter of the bronchial tube is about 3.8 mm–4.9 mm, and the outside diameter of the bronchial tube is about 4.3 mm–5.4 mm.

3. The device of claim 1, wherein the reinforcement is a wire.

4. The device of claim 3, wherein the biasing means is a spring.

5. A bronchial tube device connected to a flexible, hollow stylet defining a proximal end and an open distal end and a flexible Y-guide device for insertion into a patient's bronchial tree defining a tracheal-bronchial space and a carina, the Y-guide including flexible left and right arms joined to a central tube portion defining an open proximal end mounted to the open distal end of the stylet and biasing means therebetween, the left and right arms of the Y-guide being constructed and adapted to be deflected by the carina into the corresponding left and right bronchi, and a reinforced stabilizer mounted on the left arm for isolating the left bronchial lumen from the tracheal-bronchial space and for opening the left bronchus to atmosphere through the bronchial tube, the bronchial tube being adapted to provide a passageway for air, oxygen and anesthetic gas to the patient.

6. The device of claim 5, in which the inside diameter of the bronchial tube is about 3.8 mm–4.9 mm, and the outside diameter of the bronchial tube is about 4.3 mm–5.4 mm.

7. The device of claim 6, wherein the biasing means is a spring.

8. The device of claim 6, wire reinforcement mounted along the left arm of the Y-guide and extending along the central tube portion.

9. The device of claim 5, in which the reinforced stabilizer comprises an inflation cuff thereby enabling separation of the left and right tracheal-bronchial spaces.

10. A bronchial tube device with a flexible, attached, polymeric stylet and an associated Y-guide and inflation cuff adapted for insertion through an endotracheal tube into a patient's bronchial tree, biasing means positioned between the stylet and Y-guide, the Y-guide including left and right flexible arms for deflection by a bronchial tree carina and separation into respective left and right bronchi, the inflation cuff being mounted on the left arm of the Y-guide, whereby inflation of the cuff separates the left and right tracheal bronchial spaces, thereby occluding the left bronchial space, and enabling exposure of the left bronchial space to atmospheric pressure following surgery, and deflation of the cuff enables removal of the bronchial tube from the patient.

11. The device of claim 10, comprising an enclosed wire reinforcement mounted along the left arm of the Y-guide and extending along the central tube portion.

12. The device of claim 10, in which the inside diameter of the bronchial tube is about 3.5 mm, and the outside diameter of the bronchial tube is about 9 4.3 mm–5.4 mm.

* * * * *